United States Patent [19]
Grosz

[11] 3,947,592
[45] Mar. 30, 1976

[54] TREATMENT OF OPIATE ADDICTION

[75] Inventor: Hanus J. Grosz, Indianapolis, Ind.

[73] Assignee: Indiana University Foundation, Bloomington, Ind.

[22] Filed: May 22, 1972

[21] Appl. No.: 255,587

[52] U.S. Cl. .............................. 424/330; 424/260
[51] Int. Cl.$^2$ .................................... A61K 31/135
[58] Field of Search ................................ 424/330

[56] References Cited
OTHER PUBLICATIONS

Fennessy et al., Chemical Abstracts 74: 74888y 1971.
Dimezza et al., Chemical Abstracts 74: 2435x 1971.
Murmann et al., Chemical Abstracts 66: 1370g 1967.
Physicians Desk Reference (PDR) 25 Edition 1971 pp. 565–566.
Merck Manual 11th Edition 1966, pp. 133–134.
Current Therapy, Weiner, 1970, pp. 655–658.
Merck Manual 12th Edition, 1972, pp. 1409–1463.
The Pharmacological Basis of Therapeutics, 1966, pp. 302–303.

*Primary Examiner*—Norman A. Drezin
*Attorney, Agent, or Firm*—Kirkland & Ellis

[57] ABSTRACT

Addiction to opiate drugs, e.g., heroin, is treated by administering a beta-adrenergic-receptor-blocking drug, e.g. propranolol, which is found to block the rewarding and euphoric effects of the narcotic and to prevent the recurrence of hunger for the narcotic after withdrawal with methadone.

10 Claims, No Drawings

TREATMENT OF OPIATE ADDICTION

BACKGROUND OF THE INVENTION

This invention relates to the treatment of narcotic addiction and particularly addiction to opiate drugs such as heroin.

Narcotic addiction and its treatment may be said to involve two factors. One may be considered primarily physiological and involves all the acute sickness withdrawal symptoms which occur when the narcotic drug is discontinued, including nausea, chills, nervousness, etc. The second factor may be considered both physiological and psychological and involves the immediate rewarding and euphoric effects of taking the drug, a strong desire or hunger to resume taking the drug after withdrawal, anxiety, etc.

It is known that both categories of drug addiction effects can be blocked, and withdrawal or detoxification effected, by treatment with agents, of which methadone is the most widely used. But methadone is itself addictive and its use in withdrawal is desirably restricted to treatment periods of not more than a few weeks to carry the addict through the acute withdrawal stage. Methadone is not a good agent for maintaining abstinence from the drug after withdrawal is achieved. The search continues for a satisfactory maintenance agent, for use after withdrawal with methadone, and the answer has not previously been found.

The present invention is based on the discovery that known medicaments, previously used as beta-receptor blocking agents, or beta-adrenergic blocking agents, primarily in the treatment of cardiac arrythmias, have a surprising and powerful effect in blocking major psychological effects and at least some physiological effects of opiate drugs, including particularly the immediate rewarding and euphoric effects, and recurring "hunger" for the drug. The agents effective in this way are not found to relieve the acute physiological opiate-withdrawal symptoms. Accordingly while these agents do not appear adequate alone to support withdrawal from opiate drugs, they are of use to supplement agents such as methadone in withdrawal, and more importantly, to provide a maintenance and supportive treatment following withdrawal through the acute sickness stage with such agents as methadone.

SUMMARY OF THE INVENTION

In accordance with the invention, opiate addiction is treated by the administration of any of a number of known beta-receptor-blocking agents to the addict as a supplement to withdrawal medication or as subsequent supportive and maintenance medication.

Such known beta-receptor blocking agents include, for example, those listed in the article entitled *Clinical Pharmacology of Beta-Receptor-Blocking Drugs* by C. T. Dollery, J. W. Paterson and M. E. Conolly, published in Clin. Pharmacol Ther. 10: 765–799, Nov.-Dec. 1969.

A preferred compound for use in accordance with the invention is propranolol, having the following formula:

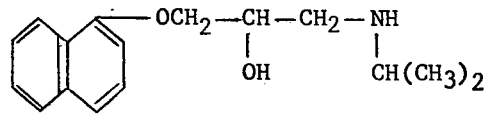

Compounds related to propranolol may be used, having modified molecular structure as represented by the following formula:

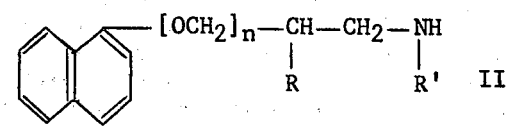

in which $n$ is zero or 1, R is H or OH, and R' is a straight or branched chain alkyl radical having from 1 to 4 carbon atoms.

In the new use, the beta-receptor-blocking agent is pre-administered, that is, administered in advance, to be present when the narcotics user administers the narcotic to himself or may be tempted to do so. The dosage may be the same as that when the agent is used for its beta-receptor-blocking effect, for example, in the case of propranolol, up to 40 mg. per day in 10 mg. oral doses. However, the narcotics blocking effect is obtained with much smaller oral dosage, for example, with propranolol in oral doses of from 5 mg. to 10 mg. per day given in either single or divided doses. Oral medication may be replaced or supplemented by injections of the agent. Dosage should be adjusted to suit the patient and his condition, and should be sufficient to produce a significant level of blocking effect against the narcotic used. The following examples illustrate the invention:

EXAMPLE I

A 27 year old white male, who had been administering heroin intravenously for over a year, has withdrawn from heroin through the use of methadone on three separate occasions. However, in each instance the patient, after apparently being successfully withdrawn, thereafter began injecting heroin. After being withdrawn from heroin for the third time the patient was instructed to ingest 10 milligrams of propranolol 4 times a day. While taking propranolol he injected himself with heroin but found that heroin now failed to elicit in him the usual and expected euphoria.

Because he kept on using heroin to alleviate the narcotic withdrawal symtoms, a fourth effort to withdraw the patient from heroin through the use of methadone was made. The patient was instructed to ingest 40 milligrams of methadone a day for the first 5 days; 30 milligrams of methadone a day for the following 4 days; and 20 milligrams of methadone per day for the last 3 days. In addition, the patient was instructed to continue to ingest 10 milligrams of propranolol 4 times a day. The patient stopped taking methadone after 7 days, but continued to take propranolol regularly for another 32 days, during which the patient was free from craving for narcotics and did not take any heroin, and at the end of which the patient decided to stop taking propranolol.

The patient reported that the propranolol blocked the immediate rewarding and euphoric effects that he usually obtained from intravenously injecting heroin, that it prvented the subsequent development of "nodding," and, also, that it prevented the recurrence of heroin hunger or craving after he was withdrawn on methadone. Propranolol also reduced his symtoms of anxiety, but it did not relieve him of his heroin abstinence symptoms, withdrawal with the help of methadone being necessary to avoid these symtoms.

EXAMPLE II

In more than 20 additional cases of heroin addiction, propranolol was administered to test for its narcotics-blocking effect, both by the present applicant and by an independent methadone treatment clinic. In some cases, it was administered concurrently with methadone; in other cases, propranolol was administered by itself. Dosages were in the range of from 10 mg. to 30 mg. per day, by mouth. The results were obtained by reports from the patients and by observations at the independent clinic. All cases confirmed the conclusions found in Example I, namely, that the administration of propranolol effectively blocked the euphoric rewarding effects of subsequently-administered heroin. At first, most hereon addicts found this surprising. They did not attribute this effect to the propranolol medication, but blamed the quantity or the quality of the heroin they had used. Some were frankly angry for having wasted their money. When further trials convinced them that the effect was produced by the medication, they all thought it would be of great help in the treatment of heroin addiction.

EXAMPLE III

A double blind study was made with a number of patients addicted to heroin. A 10 mg. per day dose of propranolol and an indistinguishable placebo were administered in random order and the patients reported the results of subsequent administration of heroin. The results confirmed the blocking effects of propranolol as described in Examples I and II.

I claim:

1. A method of blocking the euphoric rewarding effects experienced by one addicted to an opiate drug comprising administering to the addict propranolol in a dosage of at least 5 milligrams per day.
2. A method, as claimed in claim 1, wherein the propranolol is administered orally.
3. A method, as claimed in claim 2, wherein the dosage is about 10 – 40 milligrams per day.
4. A method of reducing an addict's craving for an opiate drug comprising administering to the addict propranolol in a dosage of at least 5 milligrams per day.
5. A method, as claimed in claim 4, wherein the propranolol is administered orally.
6. A method as claimed in claim 4, wherein the dosage is about 10–40 milligrams per day.
7. In the method of treating opiate addiction comprising withdrawing the addict from the opiate by administering methadone to the addict, the improvement comprising administering propranolol to the addict in a dosage of at least 5 milligrams per day at least during the period that methadone is administered in order to block the euphoric rewarding effects of the use of the opiate and to reduce the craving therefor.
8. An improvement, as claimed in claim 1, wherein the propranolol is administered orally.
9. An improvement, as claimed in claim 1, wherein the propranolol dosage is about 10 – 40 milligrams per day.
10. An improvement, as claimed in claim 1, wherein the administration of propranolol is continued after the addict is withdrawn from the opiate.

* * * * *